United States Patent [19]

Rottenberg et al.

[11] Patent Number: 4,484,582

[45] Date of Patent: Nov. 27, 1984

[54] ELECTROLYTIC FLUID FLOW RATE METHOD AND APPARATUS

[75] Inventors: David A. Rottenberg; Saul Miodownik, both of New York, N.Y.; William E. Epifanio, II, Stamford, Conn.

[73] Assignee: Memorial Hospital for Cancer & Allied Diseases, New York, N.Y.

[21] Appl. No.: 301,165

[22] Filed: Sep. 15, 1981

Related U.S. Application Data

[63] Continuation-in-part of Ser. No. 300,535, Sep. 9, 1981, abandoned, which is a continuation of Ser. No. 112,472, Jan. 16, 1980, abandoned.

[51] Int. Cl.³ .................................................. A61B 5/05
[52] U.S. Cl. ................................... 128/630; 128/691; 73/861.08; 324/446
[58] Field of Search ............... 128/630, 691, 692, 713, 128/734, 774, 642; 73/861.08; 324/439, 446, 448, 449

[56] References Cited

U.S. PATENT DOCUMENTS

| | | | |
|---|---|---|---|
| 3,078,709 | 2/1963 | Clark | 73/861.08 X |
| 3,242,729 | 3/1960 | Keller | 128/692 X |
| 3,450,984 | 6/1969 | Holmes | 73/861.08 |
| 3,566,233 | 1/1971 | Kahn et al. | 128/734 X |
| 3,592,187 | 7/1971 | Youdin et al. | 128/69 X |
| 3,798,967 | 3/1974 | Gieles et al. | 128/692 X |
| 3,820,392 | 6/1974 | Beck et al. | 73/861.08 X |
| 3,896,373 | 7/1975 | Zelby | 128/692 X |

Primary Examiner—Lee S. Cohen
Attorney, Agent, or Firm—Felfe & Lynch

[57] ABSTRACT

A system for measuring the flow rate of electrolytic fluids includes a flow cell which has a cylindrical flow channel receptive of the fluid flow to be measured and a pair of spaced apart electrodes configured to conform to the cylindrical surface of the flow channel and to be flushed therewith. The electrodes are electrically conductive and inert to the fluid of the flow and a channel is configured to effect contact of the electrodes with the fluid flow for a desired range of flow measurement. A monopolar pulse train is applied across the electrodes to effect a cell impedance across the electrodes which is inversely proportional to the rate of flow. A control signal is produced in response to the potential across the electrodes for a given unit of time and this control signal is applied to a generator for producing the monopolar pulse train in order to vary the pulse train current in the given unit of time to effect an increase in the current in response to an increase in flow rate whereby the cell impedance is stabilized for every flow rate and the electrode potential is representative of the flow rate.

12 Claims, 4 Drawing Figures

ELECTROLYTIC FLUID FLOW RATE METHOD AND APPARATUS

This application is a continuation-in-part of U.S. application Ser. No. 300,535 filed Sept. 9, 1981 and now abandoned which is, in turn, a continuation of U.S. application Ser. No. 112,472 filed Jan. 16, 1980 and now also abandoned.

BACKGROUND OF THE INVENTION

This invention relates to a method and apparatus for flow measurement and more particularly, to the measurement of very slow flow rates of electrolytic body fluids.

Numerous flowmeter devices have been proposed and developed for measuring the rate of flow of fluid through various conduits. However, the flowmeters which are commonly used for measuring relatively low flow rates fail to measure the low flow rates accurately and/or simply take too long to make the measurement.

One well-known class of flowmeters is called the head meter. It functions by measuring the pressure differential across a suitable, fixed restriction to the flow to be measured such as an orifice plate, a venturi restriction, a capillary tube or other form. the pressure differential is measured with a pressure-responsive deflectable metal diaphragm. Measurements of very, however, low flow rates suffer inaccuracies due to the history of deflection and differential pressure characteristics inherent in metal diaphragms. Morever, response time may extend to minutes or hours when the flow rate is so low that it is only capable required to flex satisfying the volume displacement of the diaphragm in minutes or hours.

Another type of flowmeter is the area type having a variable orifice and a substantially constant pressure drop rather than a fixed restriction and a varying pressure drop. In the area meter, flow rate is reflected by the changing area of the opening through which the liquid must pass maintain the constant pressure. In the area flowmeter of the type disclosed by Dettmer U.S. Pat. No. 3,712,134, a vertical tube through which the fluid is conducted in the upward direction is provided with a tapered cross-sectional area. A member therein assumes a vertical position at a condition of equilibrium between the downward gravitational force on the member and the upward pressure of the fluid flow through the variable-area annular orifice which surrounds it. The position of equilibrium is therefore a function of the flow rate; the greater the flow rate, the higher the vertical position of the float. This type of variable area flowmeter, however, cannot be used for extremely low flow rates because of the friction and other forces which load the member causing large errors in drag which distort the relationship between the flow rate and the member position and thereby give rise to inaccurate readings.

Another type of flowmeter is disclosed in U.S. Pat. No. 3,450,984. It has a pair of electrodes inserted in a fluid and a current capable of electrolyzing the fluid is passed between the electrodes. Electrolysis causes gas bubbles in the current path of the electrodes. The gas bubbles are displaced at a rate depending upon the fluid flow rate, resulting in a change in the resistance between the electrodes which is an indication of the fluid flow rate. The problem with this technique is that the response time is very, very long and reproducibility is difficult to achieve because the current between the electrodes must stabilize before an accurate measurement can be made.

The above mentioned prior art flow meters and methods of measuring flow have a further disadvantage in not being capable of adequately measuring the flow of cerebrospinal fluid in a ventriculoatrial shunt and/or a ventriculoperitoneal and lumboperitoneal shunt, the need for which measurements has increased due to the increased usage of such shunts. Cerebrospinal fluid shunt flow is particularly difficult to measure due to the intermittancy and variability of the flow caused by changes in physiological conditions. Moreover, since the shunt tubing itself is generally implanted below the skin of the patient, it is highly desirable that any flow cell associated therewith also be implantable. Lastly, due to the fact that the flow measurement is in vivo and carried out during the use of the shunt on the patient, it is important that the flowmeter itself does not in any way obstruct or change the dynamics of the flow of the spinal fluid during use.

SUMMARY OF THE INVENTION

Accordingly, it is an object of the present invention to provide a new and improved method and apparatus for measuring the flow rates of a fluid which is simple, reliable and has a fast response time.

Another object of this invention is to provide a new and novel method and apparatus for measuring slow flow rates while minimizing gross disturbances in the flow rates being measured.

Still another object of this invention is to provide a new and improved method and apparatus for measuring flow rates which are extremely slow, including the flow rates of body fluids such as cerebrospinal fluid flow rates.

A further object of the invention is to provide a new and improved flow cell which is particularly useful for the measurement of cerebrospinal fluid in a shunt, that is the flow cell does not disturb the flow rate being measured and is capable of being implanted with the shunt in a patient.

These and other objects of the present invention are achieved in accordance with the present invention by a flow cell including means forming a cylindrical flow channel receptive of the fluid flow to be measured and a pair of spaced apart electrodes which conform to the cylindrical surface of the flow channel and are flush therewith. The electrodes comprise electrically conductive material which is inert to the fluid of the flow to be measured and are configured to contact the fluid for a range related to the flow rate measurement.

In order for the flow cell to be implantable in the body, in a particularly advantageous preferred embodiment, the diameter of the flow channel is substantially equal to the diameter of the shunt tube with which it is used and the means forming the flow channel has a cylindrical outer surface, the diameter of which is substantially equal to that of the outer diameter of the shunt tube with which it is being used.

The method and device for measuring the flow rate of an electrolytic fluid through the aforesaid flow cell is based upon the belief that if a pulse is applied across the flow cell electrodes having a selected amplitude, period and pulse width or dirty cycle, electrolysis of the fluid will take place with the result that the cell impedance across the electrodes will be inversely proportional to the rate of flow. It is believed that this relationship is caused by the flow stripping electrolysis-produced bubbles from the surface of the electrodes and thus decreasing the resistance with an increase in flow rate. Also in accordance with the invention, it has been observed that as one increases the current applied across the electrodes in a given unit of time, either by increasing the amplitude or preferably by increasing the duty cycle of the pulse applied across the electrodes, the impedance will increase.

Thus, the present invention is based upon the concept that the resistance of the flow cell is directly proportional to the current applied across the electrodes in a given unit of time and inversely proportional to the rate of flow during that unit of time. Given this fact, the resistance of the flow cell can be stabilized by a negative feedback control system which varies the current applied across the electrodes in a given unit of time in response to a change in the flow rate whereupon the resulting potential across the electrodes is a direct function of the actual flow rate and is therefore representative thereof to provide a measurement value for the flow rate.

Accordingly, means for applying a monopolar pulse train across the flow cell electrodes is provided, the means being controllable to vary the current applied across the electrodes in a given unit of time in response to a control signal which preferably alters the duty cycle of the pulse train to effect an increase or decrease in current. The control signal is produced by sensing the potential across the electrodes for each given unit of time and applying the control signal as a negative feedback input to the means for applying the pulse train to effect an increase in current in response to an increase in the flow rate or a decrease in current in response to a decrease in flow rate so as to stabilize the cell impedance for each flow rate.

Since the pulse applying means and means for producing the control signal are capable of being produced by integrated circuits, the present invention makes it possible either to implant only the flow cell with the terminals of the electrodes accessible for applying the pulse train, or to implant the entire flow cell and circuitry in the patent with or without a power source therefor so that only the output of the circuit and/or the power for actuating same need be accessed or supplied.

Advantageously, a near perfect relationship between the systems output voltages and flow rates is provided. The system is also flexible enough to measure a range of flow rates which can be varied merely by altering the current density through the flow cell. Flow rates spanning more than two orders of magnitude may be measured with a given set of circuit parameters.

BRIEF DESCRIPTION OF THE DRAWINGS

The invention, together with further aspects, objects and advantageous thereof, will be better understood from the following description taken in connection with the accompanying drawings.

DESCRIPTION OF THE PREFERRED EMBODIMENTS

In accordance with the method and apparatus for measuring slow flow rates in electrolytic fluids as embodied in the present invention, the system includes two principle parts, one of which is the electrolytic flow cell through which the fluid to be measured passes and the other is the electronic circuitry to which the electrolytic flow cell is coupled for making the desired measurement.

Figure 1:
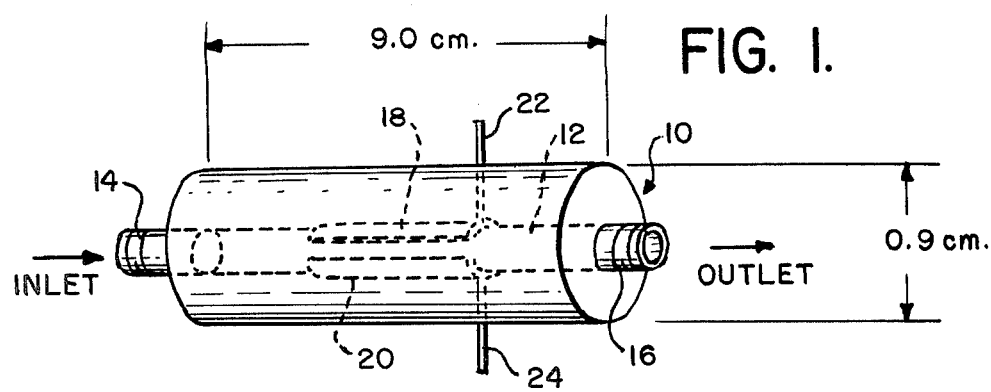
FIG. 1 is an isometric view of a flow cell which may be employed in the present invention.
Figure 2:
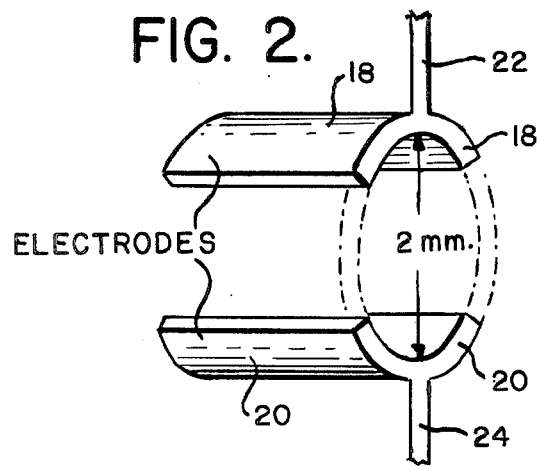
FIG. 2 is a partial enlarged view of a pair of spaced electrodes which may be utilized in the flow cell shown in FIG. 1.

Referring now to FIG. 1 and 2 which illustrate one type of flow cell which may be utilized in the present invention, the flow cell referred to generally with the reference character 10 is generally cylindrically shaped having a central channel 12 therein with an inlet port 14 on one end thereof and an outlet port 16 on the other end thereof. The fluid flow through the flow cell 10 is indicated by the arrows on the drawing in FIG. 1.

The flow cell 10 has a pair of electrodes 18 and 20 positioned parallel to each other and parallel to the external cylindrical walls of the cell. The electrodes 18 and 20 partially surround and are recessed in the channel 12 of the flow cell 10 so as to maintain contact with the fluid moving through the cell while minimizing any gross disturbances in the flow of the fluid which is being measured. Electrodes 18 and 20 have electrical contact leads 22 and 24 respectively connected thereto. The leads couple the flow cell 10 to the electronic portion of the circuitry which will be described hereinafter. The electrodes represent the only portion of the system in actual contact with the moving fluid. In order to assure the stability and reproducibility of the flow cell 10 electronic characteristics, it is important that no reactions occur at the electrode surfaces. Accordingly, gold, platinum or any other inert electrode material is preferred. The type of electrode material used will depend upon the particular application and the type of fluid being measured. All the parameters of the electrode geometry (including fluid contact range along the channel, cylindrical diameter, and spacing) affect circuit operation and accordingly the particular size and spacing will depend upon the type of measurement being made, the flow characteristics of the fluid being measured as well as other parameters for a particular application.

Figure 3:
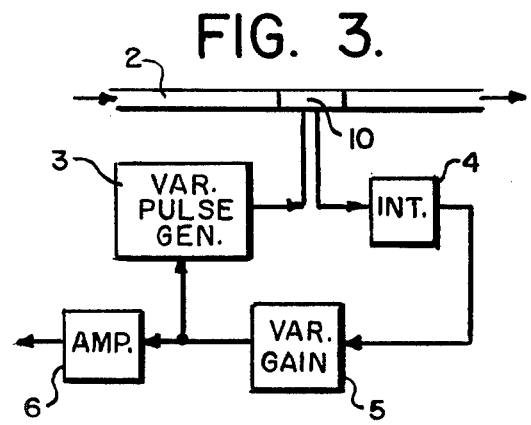
FIG. 3 is a block diagram of the system according to the invention.

FIG. 3 shows a block diagram of the system for use with the flow cell 10 for carrying out the flow measurement according to the present invention.

As shown in FIG. 3, the flow cell 10 is connected in series in a flow line 2 such as a tube or the like. The flow measuring circuitry which is attached to the electrodes of flow cell 10 comprise circuit elements 3–6. Variable pulse generator 3 applies a pulse train across the flow cell electrodes, the pulse train having a selected amplitude, period and duty cycle and the variable pulse generator 3 is capable of varying the amplitude, pulse width or period of the pulse train in order to vary the amount of current applied to the flow cell in a given unit of time. Preferably, the given unit of time is defined by a fixed period of pulses having a fixed amplitude so that the current is varied only by the pulse width per period.

The principle of the invention is based upon the fact that when a monopolar pulse is applied across the electrodes, bubbles will be formed at the electrodes in some proportion to the current applied during each period. When bubbles are formed on the electrodes, this reduces the surface area of the electrodes through which the current can pass and as a result, the impedance between the electrodes will increase, thereby reducing the current and the amount of bubbles formed. At the same time, the fluid flow itself strips away bubbles at the electrodes and the number of bubbles which are stripped away is in some way a function of the flow rate. Thus, the impedance of the flow cell is directly proportional to the current applied thereacross for each pulse period and inversely proportional to the flow rate.

At the output of the flow cell electrodes, an integrator 4 is provided which integrates the pulsed current output from the electrodes so as to obtain some dc or constant current value which will change for changes in flow rate or changes in current applied across the electrodes per period. This output from the integrator 4 is fed back to the pulse generator 3 through a variable gain element so that the amount of current per period is changed by the variable pulse generator 3 when the flow rate changes.

As can be clearly seen, since the impedence of the flow cell electrodes is directly proportional to the current per period passing therethrough and inversely proportional to the flow rate, if the flow rate should change, the current can be likewise changed to offset the change in flow rate so as to stabilize the flow cell impedance. This stabilization can be carried out relatively quickly by the negative feedback loop shown in FIG. 3.

Thus, given that there is a constant flow passing through the tube 2 for which the variable pulse generator 3 has generated a given pulse width per period which has stabilized the flow cell impedance, if the flow rate increases, the impedance of the flow cell electrodes will decrease thus increasing the steady state or constant value from integrator 4. This increase in the output of integrator 4 effects an increase in the pulse width of the pulse train being applied to the flow cell whereby the current applied to the flow cell increases and thereby the resistance thereof will increase due to increase bubble formation. Thus a constant or stabilized flow cell impedance will be achieved for this new flow rate. If the flow rate should decrease, the electrode impedance will increase thereby decreasing the output of the integrator 4 which will then decrease the width of the pulses generated by the pulse generator 3 to stabilize the impedance again.

It can be therefore recognized that the feedback control voltage applied from gain element 5 to variable pulse generator 3 is directly representative of the flow rate since it increases as the flow rate increases and decreases as the flow rate decreases and that there is a particualr value of this control voltage for each flow rate. Thus passing the control voltage through an amplifier 6 produces a signal which corresponds to the flow rate measurement and which can be displayed on a chart recorder or some digital display to indicate the actual flow rate.

Figure 4:
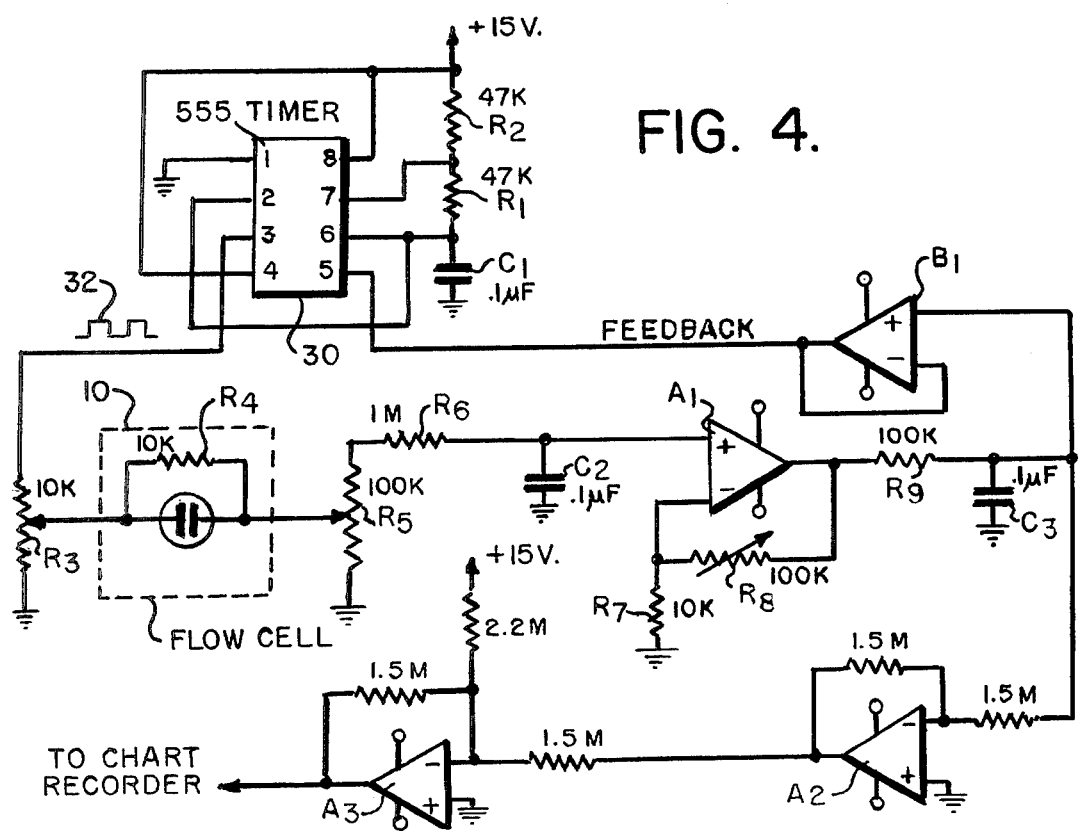
FIG. 4 is an electrical schematic diagram of an illustrative embodiment of a circuit for the system of FIG. 3.

One way of achieving the required stabilization is illustrated in one form in the electronic circuitry illustrated in FIG. 4. A monopolar pulse generator 30, illustrated in the form of a 555 integrated circuit timer chip, generates pulses 32 of a 14 volt magnitude at a frequency of approximately 100 Hz. The frequency and duty cycle of the wave form 32 are controlled by the combined values R1, R2 and C1 connected to the circuit 30 as shown as well as the voltage applied to pulse width modulation control input pin 5 which will be described hereinafter. Since the component values of R1, R2 and C1 are fixed, the pulse generator 30 relies on changes in modulation input voltage which is the signal applied to pin 5 in order to affect changes in output duty cycle and/or frequency. Accordingly, the pulse generator 30 serves as a variable pulse width pulse generator incorporating frequency and duty cycle modulation, which modulation is realized by means of changes in the input voltage which as will be explained is provided by a feedback path from the flow cell 10.

The pulse output 32 of the pulse generator 30 is applied via resistor R3 to the flow cell 10. The current flow to the flow cell 10 is controlled by resistors R3, R4 and R5. At specific flow rates, the current passing through the cell 10 can be adjusted by means of adjusting the values of resistors R3 and/or R5. The output of the flow cell taken across resistor R5 is applied to an RC network comprised of resistor R6 and capacitor C2 which integrates the pulses applied from the flow cell 10 to a dc value. This dc output, which is proportional to the current through the cell, is applied to operational amplifier A1, the gain of which is controlled by resistors R7 and R8. The output of the operational amplifier A1 is applied to an RC circuit comprised of resistor R9 and capacitor C3 which filters the output.

The filtered output from the operational amplifier A1 is applied in a feedback path through a buffer amplifier B1 to the input of the pulse generator 30. As stated before, the feedback voltage controls the output duty cycle and/or frequency of the dc pulse generator 30.

In addition, the filtered output from amplifier A1 is applied via an adding circuit comprised of amplifiers A2 and A3 which serve simply to shift the modulation voltage value onto a range which is suitable for the particular chart recorder which is being used for the measurement. The additional amplification provided by A2 and A3 does not affect the flow rate measurements and is merely utilized for simplifying data collection and the use of specific output recording devices.

The important feature in operation of the circuit described in FIGS. 3 and 4 resides in the stabilization of the impedance between the electrodes 18 and 20. This is achieved by utilizing monopolar current pulses to drive the flow cell 10 which are then integrated to a dc value and fed back to the input of the pulse generator to modulate the pulses which are applied to the flow cell. This procedure quickly stabilizes the impedance between the electrodes permitting an accurate, quick measurement to be made even for very slow flow rates. The performance of the present system can be categorized with respect to response time and the change in output voltage observed as a result of a given change in flow rate. The circuit's response time is defined as the time necessary for the impedance of the flow cell 10 to achieve the specific steady state value dictated by the flow rate present. Optimization of circuit performance involves minimizing the response time while maximizing the observed changes in output voltage which are induced by given changes in flow rates. It has been found that each of the above performances is mediated by the current density through the flow cell. At a specific flow rate as indicated above, the current passing through the cell 10 can be adjusted in accordance with the present circuit by changing the values of R3 and R5. As also been indicated, current density can be adjusted by varying the electrode geometry.

Dimensions have been provided on FIGS. 1 and 2 for the flow cell which is illustrative of a preferred form of the flow cell which may be utilized in the present invention. This specific flow cell may be utilized for an implant in the human body for measuring cerebrospinal bulk flow rates since it is the same size as the shunt tubing and can be implanted therewith. It will be appreciated that different types of cells may be utilized for different applications. Furthermore, in accordance with the present invention, the methods and apparatus provided herein may include the suspension of shaped parallel electrodes in different types of flow cells which maintain contact with the fluid being measured while minimizing disturbances with the flow rates. This is particularly required when the rates of flow are extremely slow. The magnitude of the circuit components illustrated in FIG. 4 simply constitute an illustrative embodiment for a particular application and may be varied to fit various operating requirements and environments.

If the magnitudes of the flow rates and the corresponding output voltages they induce are statistically analyzed, a near perfect logarithmic relationship results with a coefficient of determination ($R^2$) of 0.99. In accordance with the present invention, flow voltage data has been obtained covering well over two orders of magnitude for a given set of circuit component values. These limitations represent circuit limitations and not breakdowns of/or departures from the aforementioned phenomena and relationships. Specifically, flow voltage data has been obtained from a low value of 0.074 ml/min through 14 successively increasing flow values to a maximum of 24.7 ml/min. These values have also been repeatably reproducible.

It is also believed that the operation of the flow cell can be improved by coating the surface of the electrodes which contact the cerebrospinal fluid with Teflon ®. The Teflon ® coating is porous to ions and thus would not hamper the passage of current, while at the same time the coating would block proteins in the cerebrospinal fluid. It is believed that the proteins contribute to a major portion of the error in the flow measurements.

Since other changes and modifications varied to fit particular operating requirements and environments will be apparent to those skilled in the art, the invention is not considered limited to the examples chosen for purposes of illustration, and covers all changes and modifications which do not constitute a departure from the true spirit and scope of this invention.

What is claimed is:

1. A device for measuring the flow rate of an electrolytic fluid, comprising:

a flow cell including means forming a flow channel with a cylindrical surface for receiving the fluid and a pair of spaced apart electrodes conformed to the cylindrical surface of the flow channel and flush therewith for contact with the fluid, the electrodes comprising electrically conductive material which is inert to the fluid and having a geometry comprising the distance they are spaced apart, their circumferential width about the cylindrical surface to which they are conformed, and their range along the flow channel;

pulse means applying across the flow cell electrodes a train of monopolar pulses having an amplitude, period and pulse width selected in relation to the geometry of the electrodes for effecting an impedance across the electrodes which is inversely proportional to the flow rate of the fluid, the pulse means including means for varying the current of the train of monopolar pulses applied across the electrodes in a given unit of time in response to control signal applied thereto; and means for producing the control signal in proportion to the potential across the electrodes in an immediately-preceding given unit of time, for applying the control signal to the means for varying the current in a way to increase the current in response to an increase in the flow rate, whereby the cell impedance is stabilized, and for providing the control signal as a measurement representative of the flow rate.

2. The device according to claim 1, for the measurement of cerebrospinal fluid shunt flow, wherein the means forming a cylindrical flow channel includes inlet means and outlet means for connecting same in series with a cerebrospinal fluid shunt tube, a cylindrical outer surface substantially equal in diameter to the outside diameter of the shunt tube and the inner diameter of the flow channel is substantially equal in diameter to the inner diameter of the shunt tube, whereby the flow cell is surgically implantable with the shunt.

3. The device according to claim 1 or 2, wherein the pulse means comprises a variable pulse generator and the means for producing the control signal comprises an integrator and a variable gain amplifier.

4. A method of measuring the flow rate of an electrolytic fluid, comprising the steps of:

a. connecting a flow cell having a cylindrical flow channel in series with the fluid flow;

b. providing a pair of spaced apart electrodes conformed to the cylindrical surface of the flow channel and flush therewith and comprising an electrically conductive material which is inert to the fluid and having a geometry comprising the distance they are spaced apart, their circumferential width about the cylindrical surface to which they are conformed, and their range along the flow channel;

c. applying a current across the flow cell electrodes of a train of monopolar pulses having an amplitude, period and pulse width selected in relation to the geometry of the electrodes to effect a cell impedance across the electrodes which is inversely proportional to the rate of flow;

d. producing a control signal in response to the potential from the current and impedance across the electrodes in a given unit of time;

e. varying the pulse train current with the control signal to effect an increase in the current in response to an increase in the flow rate whereby the cell impedance is stabilized for every flow rate; and f. providing the potential from the current and impedance across the electrodes as a signal representative of the flow rate.

5. The method according to claim 4, for the measurement of cerebrospinal fluid shunt flow, comprising: connecting shunt tubing to a patient to establish a cerebrospinal fluid shunt, forming the flow cell with a cylindrical outer diameter substantially equal to that of the shunt tubing and the flow channel therein with an inner diameter substantially equal to the inner diameter of the shunt tubing, and connecting the flow cell in series with the shunt tubing.

6. The method according to claim 5, further comprising implanting the flow cell in the patient with the shunt tubing.

7. Apparatus for measuring a flow rate of a fluid which conducts electrical current, comprising:

an electrolytic flow cell having channel means for passing therethrough said fluid said flow rate of which is to be measured, said channel means having a pair of spaced electrodes adapted to contact said fluid passing through said flow cell, pulse generator means for controllably providing direct current pulses to said electrodes of said flow cell, means for deriving a direct current output from said electrodes proportional to the current flow through said electrodes, and feedback means coupling said direct current output to said pulse generator means and controlling said direct current pulses provided thereby for stabilizing the direct current flow between said electrodes so that a flow rate measurement can be made and providing said direct current output for said measurement of said flow rate of said fluid.

8. The apparatus set forth in claim 7, in which said flow cell comprises an enclosed body having a channel therethrough through which said fluid passes.

9. The apparatus set forth in claim 8, in which said electrodes conform to the shape of said channel and are recessed therein.

10. The apparatus set forth in claim 8, in which said pulse generator means has a variable frequency and duty cycle which is controlled by said feedback means.

11. The apparatus set forth in claim 7 in which said pulse generator means controllably provides the frequency and duty cycle of said direct current pulses, both of which are controlled by said feedback means.

12. A method of measuring a slow flow rate of an electrolytic fluid in contact with and flowing past a pair of spaced electrodes, comprising the steps of:

providing controllably pulsed direct current from a controllable d.c. pulse generator, applying said controllably pulsed direct current across said electrodes, detecting and amplifying the output from said electrodes for providing said measurement of said flow rate of said fluid, and controlling and controllably pulsed direct current applied across said electrodes by feeding said detected and amplified output from said electrodes back to said controllable d.c. pulse generator for stabilizing said current applied across said electrodes.

* * * * *

UNITED STATES PATENT AND TRADEMARK OFFICE
CERTIFICATE OF CORRECTION

PATENT NO. : 4,484,582
DATED : Nov. 27, 1984
INVENTOR(S) : D.A. Rottenberg, et al.

It is certified that error appears in the above-identified patent and that said Letters Patent is hereby corrected as shown below:

Claim 12, line 11 "and" should be -- said --.

Signed and Sealed this

Sixth Day of August 1985

[SEAL]

Attest:

DONALD J. QUIGG

Attesting Officer

Acting Commissioner of Patents and Trademarks